United States Patent

Pobo

[11] Patent Number: 6,011,523
[45] Date of Patent: Jan. 4, 2000

[54] DEVICE FOR CONTROLLING OSCILLATING ELECTROMAGNETIC FIELDS, IN PARTICULAR RADIO WAVES

[76] Inventor: Franz Pobo, Mariaberger Strasse 241, Kempten, Germany, D-87439

[21] Appl. No.: 08/765,118
[22] PCT Filed: Jun. 6, 1995
[86] PCT No.: PCT/EP95/02162
  § 371 Date: Jan. 28, 1997
  § 102(e) Date: Jan. 28, 1997
[87] PCT Pub. No.: WO95/33515
  PCT Pub. Date: Dec. 14, 1995

[30] Foreign Application Priority Data

Jun. 6, 1994 [DE] Germany .......................... 94 09 130 U
Apr. 27, 1995 [DE] Germany .......................... 295 07 121 U

[51] Int. Cl.⁷ .................................................. H01Q 1/52
[52] U.S. Cl. ........................... 343/841; 343/867; 324/244
[58] Field of Search ................................. 343/840, 841, 343/867, 866, 868, 741, 742; 333/175; 324/318, 319, 244, 241.1; H01Q 1/52

[56] References Cited

U.S. PATENT DOCUMENTS

| | | | |
|---|---|---|---|
| 4,587,487 | 5/1986 | Zanzucchi | 324/244 |
| 5,752,514 | 5/1998 | Okamura et al. | 128/653.1 |

FOREIGN PATENT DOCUMENTS

| | | |
|---|---|---|
| A 511 781 | 6/1952 | Belgium . |
| A 0 130 474 | 1/1985 | European Pat. Off. . |
| A 3 900 652 | 6/1990 | Germany . |
| A 4 014 118 | 11/1991 | Germany . |
| A 4 110 030 | 1/1992 | Germany . |
| 295 02 054 U | 5/1995 | Germany . |

*Primary Examiner*—Don Wong
*Assistant Examiner*—Tho Phan
*Attorney, Agent, or Firm*—Knobbe, Martens, Olson & Bear, LLP

[57] ABSTRACT

In order to provide a device for the control of oscillating electromagnetic fields, in particular those from mobile radio transmitters, so that detrimental frequency intensity spectra are converted into largely innocuous spectra, the invention proposes that the oscillator coils are disposed parallel to each other and at least one container filled with a powder mixture is disposed longitudinal side of the oscillator coils.

20 Claims, 3 Drawing Sheets

DEVICE FOR CONTROLLING OSCILLATING ELECTROMAGNETIC FIELDS, IN PARTICULAR RADIO WAVES

BACKGROUND OF THE INVENTION (1) Field of the Invention

The invention relates to a device for controlling oscillating electromagnetic fields, particularly radio waves, according to the preamble of claim 1.

(2) Description of the Related Art

Such a device is already known from European Patent 130 474, in which in particular it is intended to attenuate the effect of magnetic fields with the aid of pulsating direct current. In order to attenuate magnetic fields such as occur in directional tranmitters or directional emitters, it is here proposed to radiate the pulses with a frequency in the range between 1 and 10,000 Hz into the region of the earth's surface and the atmosphere adjoining it. In order to generate such a weak magnetic field a transmitter is provided with an antenna for generating pulsating direct current at the above named frequency. In this case the transmitter is preferably connected to a rectifier which may be connected via a mains transformer to a source of alternating current. This transmitting apparatus further has a transmitting antenna in order to attenuate the effect of magnetic fields in a range of approximately 100 m in the environment of the generated radiation.

In this case however it is disadvantageous that the screening apparatus is connected to the mains voltage of 220 V, so that mains-independent operation is not possible. In addition, a specific frequency is set, so that this device cannot adapt to alternating oscillating electromagnetic fields, but must on every occasion be newly adjusted. Thus use of such a screening apparatus becomes complex and its effectiveness is lessened. This is of particular importance as the environment is permeated by a plurality of different radio signals and oscillating electromagnetic fields. These are generated by data transmission installations, radar installations, radio and television transmitters, information satellites, radio devices and the like. In particular, microwave ovens and mobile telephones contribute to such electromagnetic load, which is known by the title of electrosmog, and can lead to a considerable stress on living creatures, particularly due to the increasing extension of mobile telephone networks.

The digital and analog wave length ranges generated by blanket-coverage transmitter installations can lead to considerable damage such for example as permanent stress. It is impossible to escape from this so-called electrosmog, as the effect of these waves is universal and uninterrupted. The intensity does in fact reduce with distance, but it is still X times stronger than the voltage in cells of the human body.

It is of particular importance here that the biochemical processes in the human body are controlled by ultrafine electromagnetic signals, a power of 0.00.1 $mW/cm^2$ being used for transmitting information to membrane structures. For this discovery of the so-called ion channels, the Nobel prize for medicine was awarded for example in the year 1991. On the other hand, during use of a mobile telephone, in part power levels of 2,000 and more $mW/cm^2$ are used. Thus for example considerable stress can be exerted for example on the pineal body, but also on other organs and nerve cells. In order to receive such waves which are not guided, antenna systems are necessary which for example are formed by the DNA, the nerve cell extensions or the vascular stem of the brain. Thus living creatures can be disturbed over a long period. Thus the frequency of approximately 500–900 MHz such as is used for mobile telephone networks, can cause an alteration in the brain current of the human which can be indicated by EEG. At a power level of 0.1 $mW/cm^2$, such as is intended to be achieved in a blanket-coverage manner by the completion of the D-mobile network, biological processes can already be considerably disturbed.

The derivation of electromagnetic waves with the aid of two interconnected main-independent coils is known from DE 40 14 118 A1. A disadvantage in this case however is that only a frequency range of the electromagnetic radiation can be attenuated, so that the effectiveness is low. In addition the coil system must be directly connected with the object to be protected, which can scarcely be achieved in the case of persons.

SUMMARY OF THE INVENTION

It is therefore the object of the invention to provide a device which reduces damaging spectra of electromagnetic oscillations in a simple and compact form.

This object is achieved by the device according to the features of claim 1.

According to the invention, by means of the arrangement proposed of a plurality of oscillator coil and a special powder mixture in the vicinity of the oscillator coils, a resonant circuit is formed, which brings the frequency intensity spectrum occurring in mobile telephone transmitters or microwave ovens closer to the frequency intensity spectrum which occurs terrestrially or naturally. The device, contained in a casing, for controlling oscillating electromagnetic fields, thus operates in a mains-independent manner, as it directly absorbs the energy contained in the oscillating electromagnetic field and converts it. This conversion is effected with automatic adaptation to the frequency obtaining at any time of the environmental field. In this way a considerable compensation or balancing of external interference fields is achieved. Due to its compact structure, the device can be stored in a compact way, e.g. in a cabinet, but also in the vicinity of the body, e.g. in a sports bag or a handbag.

Further advantageous features are the subject matter of the sub-claims.

BRIEF DESCRIPTION OF THE DRAWINGS

Three embodiments given by way of example will be described and explained in the following with reference to the drawings, which show.

DESCRIPTION OF THE PREFERRED EMBODIMENT

Figure 1:
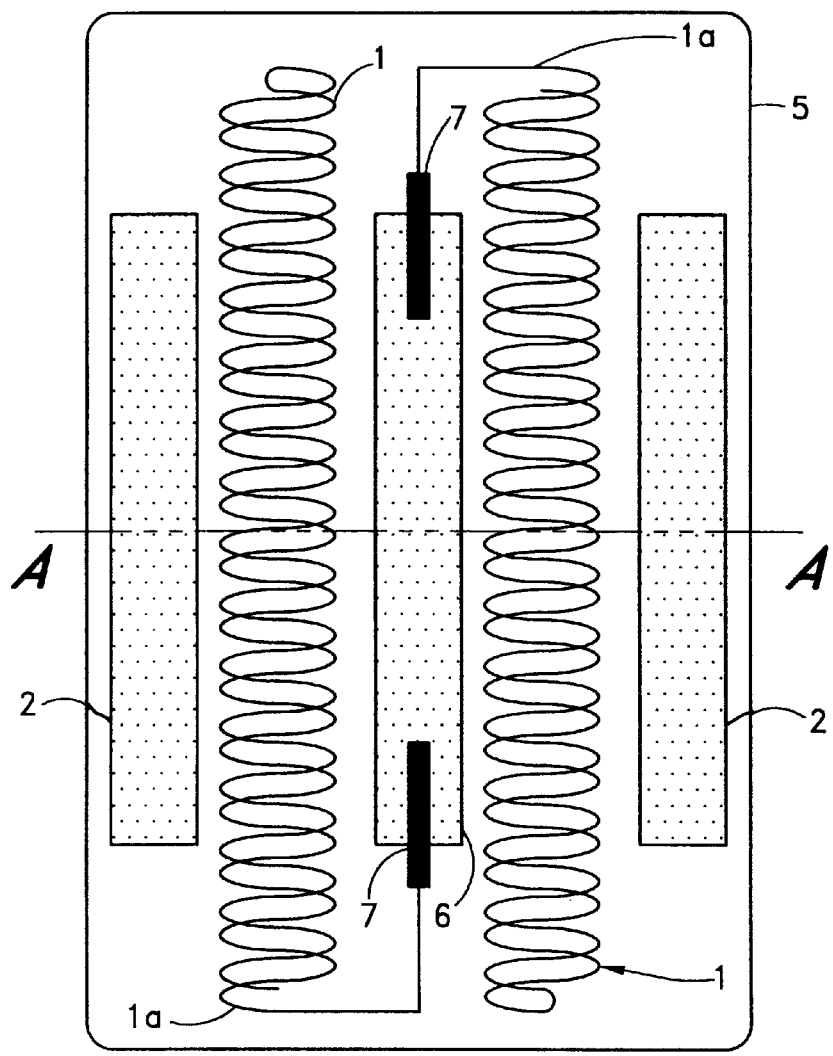
FIGS. 1 and 3: respective plan views of a device for controlling an electromagnetic field of oscillation.
Figure 2:
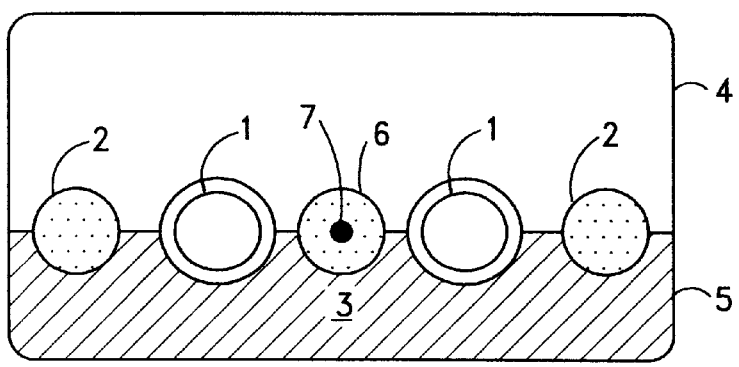
FIGS. 2 and 4: associated cross-sections shown respectively according to FIGS. 1 and 3 along lines A—A, and FIGS. 5 and 6 a further embodiment, disposed upright.

A preferred, particularly compact and thus easily carried embodiment with two oscillator coils 1 is shown in FIGS. 1 and 2. A powder mixture shown in black is disposed in the vicinity of the oscillator coils 1 in containers 2 and 6. These containers in this case are in the form of tube 2, 6, the central glass tube 6 being connected to two electrodes 7. The axes of these components 1, 2 and 6 are aligned parallel to one another, and the oscillator coils 1, which are wound in contrary directions, are connected by means of soldered points to the pin-shaped electrodes 7 of the centrally-located tube 6. The oscillator coils 1 project at both ends over the powder-filled tubes 2, 6, which fit flush with one another. The oscillator coils 1 are formed by thin silvered copper wires with bifilar windings of 9.0 mm, preferably have twelve windings, the oscillator coils 1, arranged in pairs, being repectively wound in an opposed manner (i.e. right-hand or left-hand) and being connected by their free ends 1a to the electrodes 7 projecting into the central tube 6.

These oscillator coils are caused to oscillate by the external oscillating electromagnetic field, e.g. by radio waves, and therefore are oscillated automatically. Thus there arises a field of oscillation in the region of the oscillator coils 1, of the adjoining parallel-arranged powder mixture tube 2 and of the centrally located powder mixture tube 6 with the inserted electrode 7. This field of oscillation, with a frequency and intensity depending on the environmental field, is thus effected by the powder mixture in the glass tubes 2 and 6, glass or acrylic glass being preferably usable as a material for the tubes 2 and 6.

A factor of considerable importance in this respect is the composition of the powder mixture. Preferred compositions contain powder of various crystal lattices (cuboid, hexagonal, tetragonal, orthorhombic, monoclinic, triclinic and trigonal) and containing a plurality of quartz minerals. Such a preferred powder mixture can be of the following preferred composition:

12 parts: Cu 3 parts each: Fe, rock crystal, amethyst 1 part each: Al, Sn, Ag, Au, rhodonite, ruby, onyx, garnet, azurite A tube 2 or 6 contains approximately 6 to 8 g of this powder mixture, so that the overall quantity in this construction comes to approximately 20 g.

Due to this composition of the powder mixture in the tubes 2 and 6 the electromagnetic field detected by the resonant circuit with the oscillator coils 1 is affected, on the one hand the external electromagnetic field being attenuated and approximated by resonance to the naturally occurring frequency intensity spectrum. In particular by means of the powder mixture described above with the components of various crystal lattices, a specific frequency such for example as 900 MHz in mobile telephone networks is split up, so that a wide, extensibly harmless frequency spectrum is achieved, particularly as, by means of phase displacement, an extensive superimposition and thus extinguishing of the negative or positive amplitudes results.

The construction described above with the oscillator coils 1 arranged in parallel, which are capacitively interconnected by the electrodes 7, and are surrounded by the powder mixture tubes 2, 6 disposed centrally and externally on their longitudinal sides, is embedded in a silicone compound 3 and housed in a rectangular casing lower portion 5, as shown in cross-section in FIG. 2. The casing lower portion 5 is closed from the top by a plastic cover as a casing upper portion 4. In order for example to protect the device from chemicals in the environment, the casing portions 4, 5 may be welded together. There may also be formed in the casing lower portion 5 a cup-shaped parabolic reflector, which concentrates the occurring field of oscillation towards the centre, in this case towards the central glass tube 6 or the powder mixture contained therein.

The device thus formed is suitable for the direct living environment of the human being and may for example be set up in the house or individual rooms or in a car, in order to avoid damaging biological effect. This compact apparatus may in particular be carried directly on the person, e.g. in pockets or garments. Here also it serves for successful and permanent reinforcement after biorythms therapies. In this case the device is set up in the vicinity of oscillation generators, for example in the vicinity of a radio telephone or microwave oven. In this way the transmission radiation and thus radiation stress for human, animal and plants is reduced to a harmless level. Several such devices may also be combined. By altering the powder mixture, for example increasing the ingredients with a hexagonal crystal lattice (tin grain), an individual adaptation to the oscillating electromagnetic field occurring at any time can be achieved.

Figure 3:
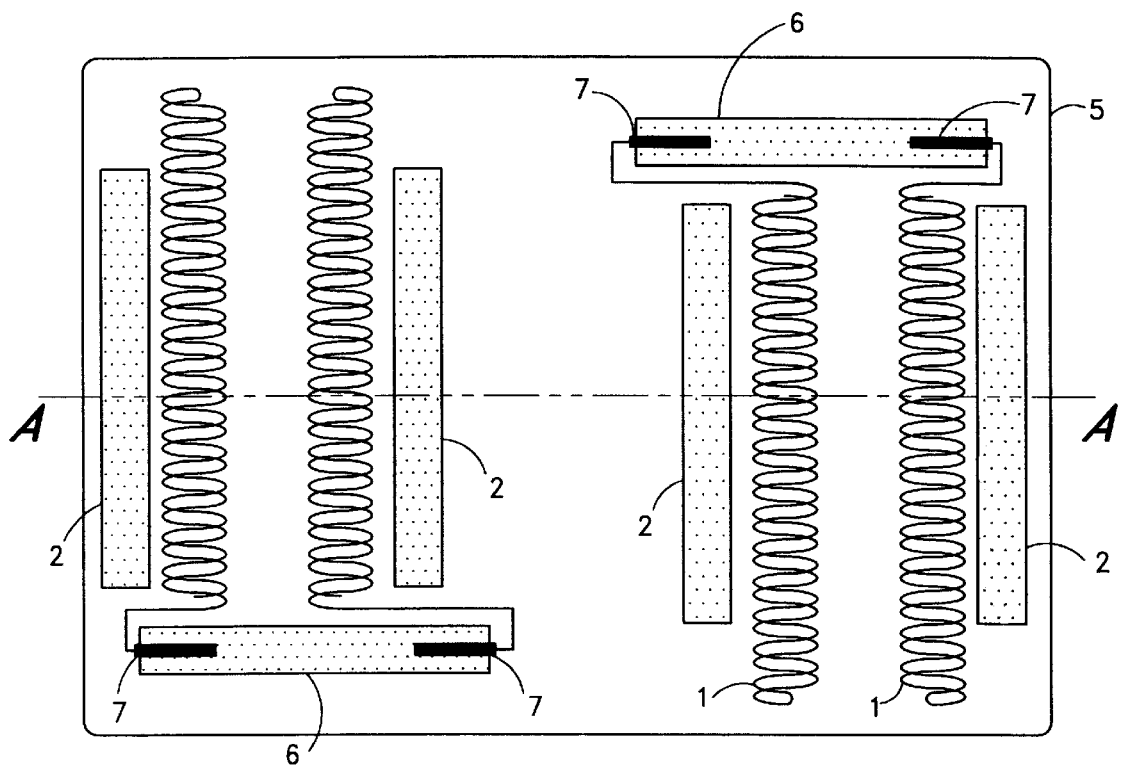
Figure 4:
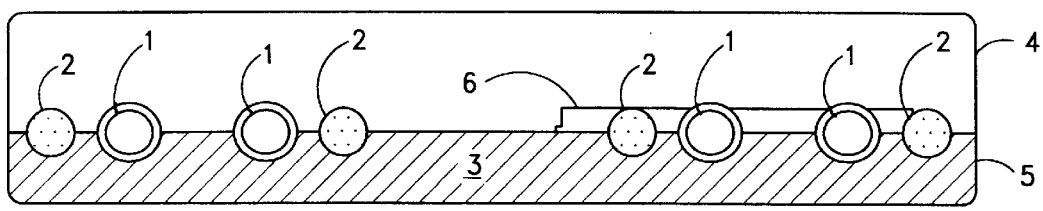

An extended embodiment is shown in FIGS. 3 and 4, in which, in one plane, four oscillator coils 1 and four powder tubes 2 in a parallel alignment thereto and two powder tubes 6 are embedded vertically thereto in a silicone compound 3, so that two units arranged symmetrically with one another results. In each unit there are located between two tubes 2 filled with the powder mixture described above shown in black or in dots in cross-section, in each case two oscillator coils 1 disposed in a mirror image to one another due to the winding direction, and which fit at their ends 1a flush with the tubes 2 in one series and at these free ends 1a are connected to the central glass tube 6 disposed transversely thereto, at its copper electrode 7. At the other upper end, here on the left hand, they project in the common plane beyond the tubes 2 form a flush connection with the central glass tube 6 of the other unit, here on the right. The double unit is in turn housed by means of an embedding compound 3, (particularly silicone) in a casing lower portion 5, which preferably has a transparent cover 4.

Figure 5:
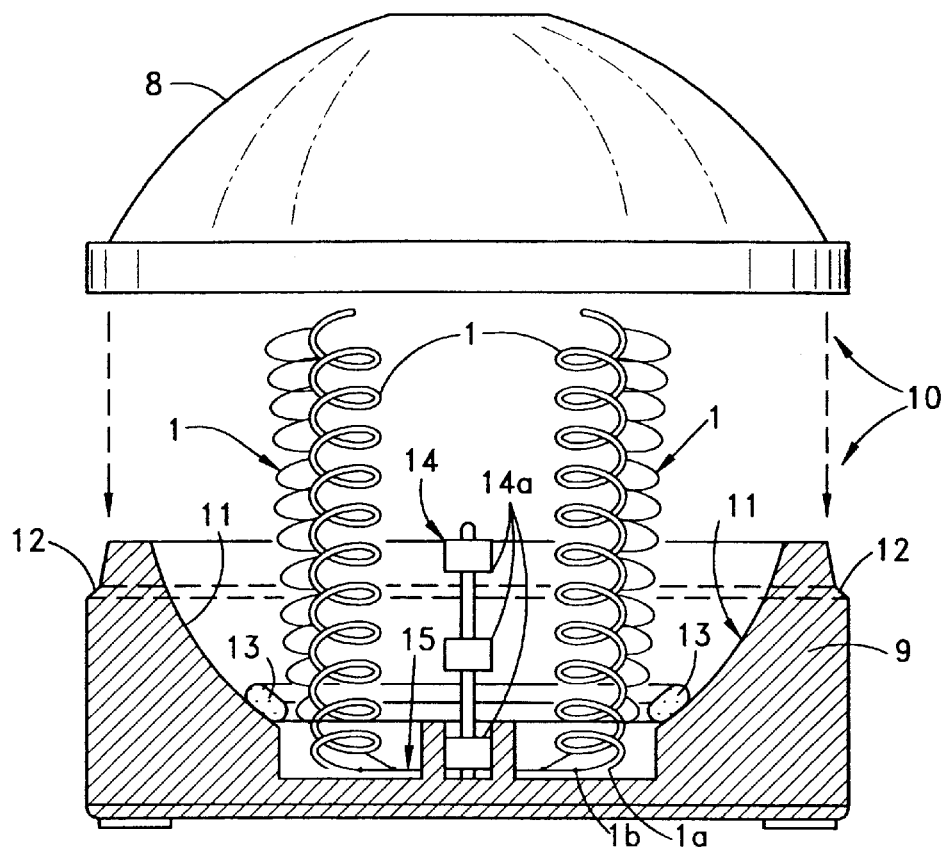
Figure 6:
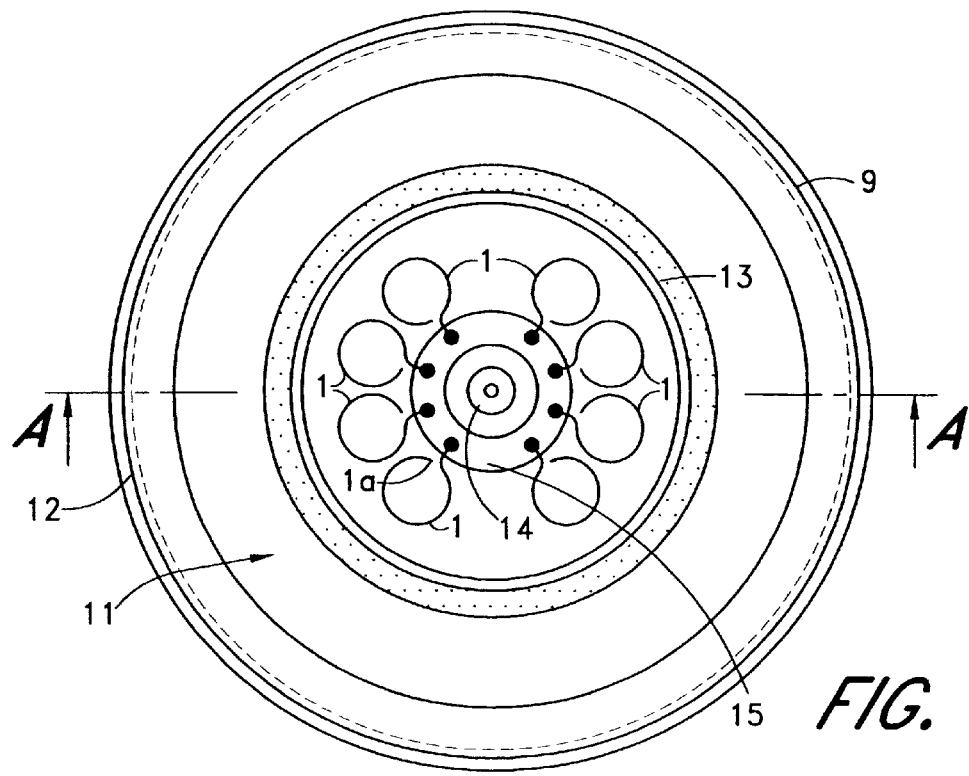

FIGS. 5 and 6 show a further embodiment which, contrary to the previous embodiments which were disposed flat, has upright oscillator coils 1. In this case eight oscillator coils 1 are arranged point-symmetrically to the centre, their axes of rotation extending parallel to one another. The oscillator coils 1 are in turn formed by thin, silvered copper wires with bifilar windings, and preferably have twelve winding. One end 1b of the winding is free in each case and respectively wound in an opposed direction (i.e. right-hand or left-hand).

These oscillator coils 1 are in turn excited by the external oscillating electromagnetic field, for example by radio waves, and thus are themselves brought into high-frequency oscillation, yet with an altered amplitude and phase configuration. In co-operation with a magnet 14, which in a preferred construction is located centrally, and which in this case is formed by three permanent magnets 14a arranged one above the other, there thus results a resonant circuit responding to the field of oscillation in the vicinity of the oscillator coils 1. This field of oscillation, with a frequency and intensity dependent on the environmental field, is in this case considerably affected by a ring 13, as a powder container, and surrounding the oscillator coils, and which corresponds in its method of operation to the tubes 2 and 6 described above, as this external ring 13 (shown in dotted lines) also contains a powder mixture as described above, which contains at least one metal component and crystals of varying crystal lattices. The ring 13 contains approximately 25 g of this powder mixture and has a transparent tube as an outer cover.

By means of this composition of the outer ring 13 there is an influence on oscillation, particularly a phase displacement of the magnetic field detected by the oscillator coils 1, on the one hand the outer magnetic field being attenuated and approximated by a resonance to the naturally-occurring frequency intensity spectrum. In particular by means of the powder mixture described above with the components of various crystal lattices, a specific frequency is split up, so that instead of it, a wide, largely harmless frequency spectrum with reduced amplitudes is achieved.

The structure described above with the oscillator coils 1 arranged upright, which are interconnected by a connecting ring 15 and surround the centrally-located magnet 14, and surrounded by the external ring 13 containing the powder mixture, is housed in a spherical casing 10. The resultant symmetrical structure is particularly visible is FIG. 6. The encapsulated casing 10 comprises a shell-shaped lower portion 9, which is closed from the above by a hood 8 as a casing upper portion. In this case the hood is shown removed, but in operation is mounted in accordance with the arrows shown in dotted lines. There is formed in the casing lower portion a cup-shaped parabolic reflector 11, which concentrates the occurring field of oscillation towards the centre. At the point of connection between lower portion 9 and hood 8 there is provided a continuous groove 12, into which there engages a correpondingly-shaped bead of the hood 8, after it has been mounted, so that the casing 10 of the device is splash-proof.

The device thus formed with the casing 10 is mounted in particular directly on the oscillating generator, for example on a transmitting tower in the vicinity of the antenna installation. In this way the radiation emission in the vicinity of the ground is reduced, thus also reducing radiation stress for humans, animals and plants to a harmless level. A plurality of such devices may be incorporated in series, as shown in principle in the construction according to FIGS. 3 and 4. By changing the powder mixture in the tubes 2 and 6 or the ring 13, individual adaptation can thus be achieved to the oscillating electromagnetic fields present at any time. A factor of particular importance is that the device for controlling oscillating electromagnetic fields operates in a mains-independent manner, as it directly absorbs and converts the energy contained in the oscillating electromagnetic field. In this case this conversion is effected with automatic adaptation to the frequency of the environmental field obtaining at any moment. Thus a considerable compensation or balancing of external interference fields is achieved.

It should be noted that, instead of the preferred arrangement on the transmitters and thus on the causes of disturbing oscillating electromagnetic fields, the electromagnetic device can also be set up in the direct living area of the person, thus for example in the house or in individual rooms, in order to avoid damaging biological effects. Likewise, instead of the powder-filled ring 13, the tubes 2 and 6 shown in FIGS. 1 to 4 may also be disposed parallel to the oscillator coils 1 in the spherical casing 10.

I claim:

1. A device for controlling oscillating electromagnetic fields comprising:
   interconnected oscillator coils, said oscillator coils being disposed parallel to one another, and at least one container containing a powder mixture being disposed on at least one longitudinal side of said oscillator coils.

2. The device according to claim 1, wherein said containers are in the form of tubes.

3. The device according to claim 1, wherein said oscillator coils and said powder mixture containers are aligned parallel to one another.

4. The device according to claim 1, wherein said container coupling two oscillator coils in each case has two mutually-opposite electrodes each of which is connected to a coil end.

5. The device according to claim 1, wherein said oscillator coils and said powder mixture containers are respectively disposed symmetrically and in pairs relative to one another.

6. The device according to claim 1, wherein said oscillator coils each have a plurality of windings and are non-conductively coupled to one another.

7. The device according to claim 1, wherein said oscillator coils are formed from silvered copper wire.

8. The device according to claim 1, wherein said powder mixture containers are filled with a plurality of quartz minerals.

9. The device according to claim 1, wherein said containers are filled with powders of various crystal lattices, particularly with the following composition: 12 parts Cu; 3 parts each: Fe, rock crystal, amethyst; 1 part each: Al, Sn, Ag, Au, rhodonite, ruby, onyx, garnet, azurite.

10. The device according to claim 1, wherein a glass or plastic casing is provided for containing the powder mixture.

11. The device according to claim 10, wherein a plastic cover is provided and is connected to a lower portion of said casing.

12. The device according to claim 10, wherein said powder mixture is cast in a silicone compound and is adjusted in said casing.

13. The device according to claim 12, wherein said silicone compound extends as far as a central plane of said powder mixture disposed in one plane.

14. The device according to claim 10, wherein a cup-shaped parabolic reflector is located in said casing.

15. The device according to claim 1, wherein said container for said powder mixture is in the form of a ring.

16. The device according to claim 1, wherein said containers are filled in the range of 50 to 100% with said powder mixture.

17. The device according to claim 1, wherein the overall quantity of said powder mixture is between 10 to 25 g.

18. The device according to claim 1, wherein said oscillator coils each have a bifilar winding wound and aligned in an opposite direction.

19. The device according to claim 1, wherein said oscillator coils stand upright and are attached to a connecting ring.

20. The device according to claim 19, wherein said oscillator coils surround a centrally-located magnet.

* * * * *